US006593388B2

(12) United States Patent
Crivello

(10) Patent No.: US 6,593,388 B2
(45) Date of Patent: Jul. 15, 2003

(54) OLIGOMERIC AND POLYMERIC PHOTOSENSITIZERS COMPRISING A POLYNUCLEAR AROMATIC GROUP

(75) Inventor: James V. Crivello, Clifton Park, NY (US)

(73) Assignee: Renssealer Polytechnic Institute, Troy, MI (US)

( * ) Notice: Subject to any disclaimer, the term of this patent is extended or adjusted under 35 U.S.C. 154(b) by 11 days.

(21) Appl. No.: 09/826,330

(22) Filed: Apr. 4, 2001

(65) Prior Publication Data

US 2002/0025991 A1 Feb. 28, 2002

Related U.S. Application Data

(60) Provisional application No. 60/194,455, filed on Apr. 4, 2000.

(51) Int. Cl.[7] .................... C08F 2/50; C08G 65/00; G03F 7/029
(52) U.S. Cl. ............... 522/25; 522/148; 522/168; 522/170; 522/181; 430/2; 430/269; 430/280.1; 430/281.1
(58) Field of Search .................. 522/26, 50, 53, 522/59, 63, 68, 125, 126, 127, 129, 167, 170, 181, 182, 188, 904, 35, 25, 7, 31, 148, 120, 168; 430/2, 269, 280.1, 281.1

(56) References Cited

U.S. PATENT DOCUMENTS

| 3,591,661 | A | * | 7/1971 | Rogers, Jr. .................. 522/112 |
| 4,058,400 | A | * | 11/1977 | Crivello .................. 430/286.1 |
| 4,921,589 | A | * | 5/1990 | Yates et al. ............. 204/157.15 |
| 6,093,753 | A | * | 7/2000 | Takahashi ................. 430/280.1 |
| 6,313,188 | B1 | * | 11/2001 | Takahashi ................... 522/168 |

FOREIGN PATENT DOCUMENTS

| JP | WO97/08141 | * | 3/1997 |
| JP | WO98/12232 | * | 3/1998 |

\* cited by examiner

Primary Examiner—Susan W. Berman
(74) Attorney, Agent, or Firm—Heslin Rothenberg Farley and Mesiti P.C.; Mary Louise Gioeni, Esq.

(57) ABSTRACT

Enhancement of the rates of cationic polymerizations initiated by onium salts has been achieved through the use of oligomeric and polymeric electron-transfer photosensitizers derived from a polymerizable compound substituted with a polynuclear aromatic group, including epoxides, oxetanes, and ethylenically unsaturated compounds. The polymerizable compound is substituted with residues derived from anthracene, naphthalene, perylene, pyrene, fluorene, carbazole, indole, benzocarbazole, acridone, phenothiazine, and thianthrene, particularly carbazole.

52 Claims, 5 Drawing Sheets

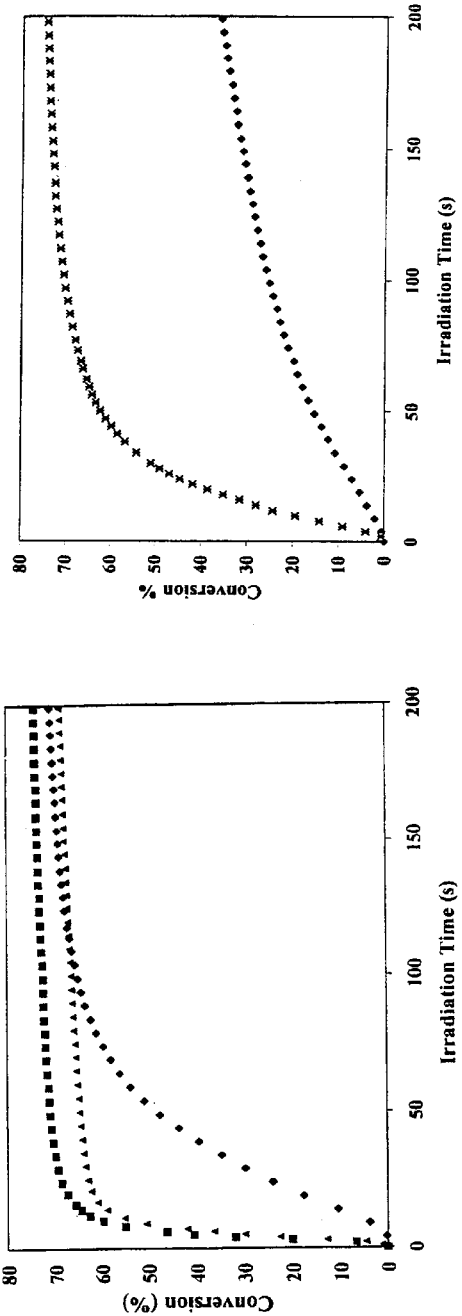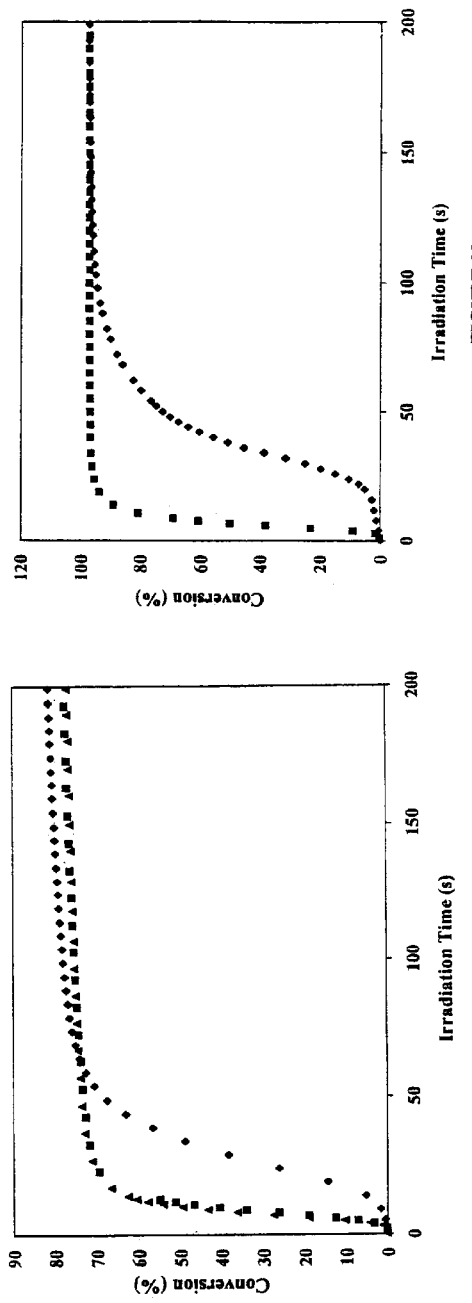

OLIGOMERIC AND POLYMERIC PHOTOSENSITIZERS COMPRISING A POLYNUCLEAR AROMATIC GROUP

CROSS-REFERENCE TO RELATED APPLICATIONS

This application claims the benefit of U.S. Provisional Application No. 60/194,455, filed Apr. 4, 2000.

FIELD OF THE INVENTION

The invention relates to oligomeric photosensitizers for use in cationic photopolymerizations.

BACKGROUND OF THE INVENTION

Cationic polymerization is employed in many commercially important applications, including, for example, decorative and abrasion resistant coatings, printing inks, adhesives, fiber reinforced composites, microelectronic encapsulations, tan coatings, pressure sensitive adhesives, high performance aerospace composites, fiber optic coatings, stereolithography, photoresist and holographic recording media. The term "UV cure" has also been applied to such processes because the polymerizations are typically induced by light having a wavelength in UV region below about 450 nm.

Cationically photopolymerizable, or photocurable, compositions typically contain one or more monomers or oligomers having epoxy or vital ether functionality, and a photoinitiator.

Currently, the most commonly used photoinitiators employed for photoinduced cationic ring-opening polymerizations are diaryliodonium salts, I, and triarylsulfonium salts, II, with the general structures shown below, in which $MtX_n^-$ represents a weakly nucleophilic counterion such as $BF_4^-$, $SbF_6^-$, $PF_6^-$, and $(C_6F_5)_4B^-$. Another class of photoinitiators that show considerable promise is dialkyphenacylsulfonium salts, III. (See J. V. Crivello, J. H. W. Lam, *Polymer Preprints* 1979, 20, 415.)

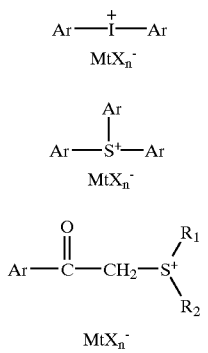

These three different types of photoinitiators possess high quantum yields of photolysis and are efficient photoinitiators of cationic polymerizations when irradiation is carried out using light in the short wavelength UV region (230–300 nm). A wide variety of vinyl and heterocyclic monomers undergo facile photoinduced cationic polymerizations using these photoinitiators.

Many of the above mentioned commercial applications of photopolymerizations are continuous, high speed web-base processes, and require correspondingly very high polymerization rates (cure speed). Therefore, there is a continuing need for highly efficient photoinitiator systems.

For maximum efficiency, the photoinitiator system must possess strongly absorbing chromophors that match as closely as possible the emission bands of the light source. The most intense emission bands of common light sources such are mercury arc lamps typically lie predominantly at wavelengths above 300 nm. However, most onium salt photoinitiators absorb most strongly at wavelengths below 250 nm.

One approach to increasing cure speed has been the use of photosensitizers to increase the response of photoinitiators to longer wavelengths. Electron-rich polynuclear aromatic compounds such as anthracene pyrene, perylene, coronene, 9,10-diphenylethynylanthracene, and carbazole compounds have been used with some success. However, these photosensitizers have serious drawbacks that limit their utility in UV cure applications. Anthracene and pyrene, for example, are volatile and can be lost during coating operations, with loss of effectiveness. Further, most polynuclear aromatic compounds (among them anthracene, pyrene, perylene, phenanthrene, and coronene) are acutely toxic, as well as potentially carcinogenic. Health and safety considerations, therefore, limit their use in many applications, especially in highly attractive food contact applications. As a result, there is a need for non-volatile and non-toxic photosensitizers.

BRIEF DESCRIPTION OF THE DRAWINGS

FIG. 17 is a photopolymerization of cyclohexene oxide in the presence of 1.0% SOC10 using 0.5% 9-(2,3-epoxypropyl)carbazole, (▲) and poly[9-(2,3-epoxypropyl) carbazole] (■). Polymerization in the absence of a photosensitizer (♦). (Light intensity 200 mJ/cm$^2$ min)

FIG. 18 is a comparison of the photosensitized polymerizations of cyclohexene oxide in the presence of 0.5% poly[9-(2,3-epoxypropyl)carbazole] (*) and in the absence of a photosensitizer (▲) using 1.0% DPS-C$_1$C$_{12}$ as the photoinitiator. (Light intensity 200 mJ/cm$^2$ min)

FIG. 19 is an RTIR study of the photosensitized polymerization of cyclohexene oxide carried out with 1.0% 9-(2-vinyloxyethyl)carbazole (■) or its polymer (▲). Polymerization carried out in the absence of a photosensitizer (♦). (1.0% IOC10 as the photoinitiator, light intensity 200 mJ/cm$^2$ min)

FIG. 20 is a photosensitized polymerization of 2-chloroethyl vinyl ether with 0.2% IOC10 alone (♦) and in the presence of 0.5% 9-(2-vinyloxyethyl)carbazole, (■) as a photosensitizer. (Light intensity 200 mJ/cm$^2$ min)

SUMMARY OF THE INVENTION

Figure 2:
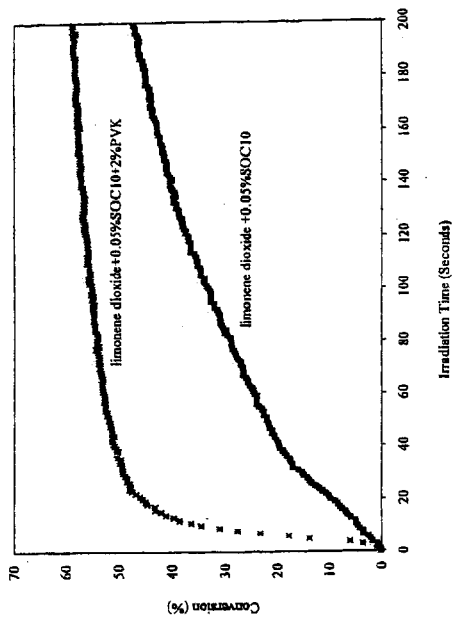
FIG. 2 is a comparison between the epoxide polymerization of limonene dioxide (LDO) alone (■) and in the presence of 2.0% 9-vinyl carbazole (NVK) (*). (Light intensity 169 mJ/cm$^2$ min; 0.05% SOC10)

The present invention relates to a method for increasing the rate of a cationic photopolymerization. The method comprises:
 a. combining
  i. a photosensitizing composition selected from the group consisting of:
   at least one polymerizable photosensitizer;
   at least one polymeric photosensitizer comprising repeating units derived from the at least the polymerizable photosensitizer;
   at least one siloxane comprising repeating units derived from a hydrosilation reaction between a SH-containing siloxane and at least one vinyl or allyl compound substituted with a polynuclear aromatic group;
   and combinations thereof;
   wherein the polynuclear aromatic group absorbs light having a wavelength ranging from 300nm and 600 nm; and
   the polymerizable photosensitizer comprises at least one polymerizable compound substituted with the polynuclear aromatic group;
  ii. at least one cationic photoinitiator comprising an onium salt; and
  iii. a cationically photopolymerizable composition; and
 b. exposing the combination to light.

In another aspect, the present invention relates to a photopolymerizable composition comprising:
 a. the photosensitizing composition described above;
 b. at least one cationic photoinitiator comprising an onium salt; and
 c. a cationically photopolymerizable composition.

In yet another aspect, the invention relates to a polymeric photosensitizer comprising repeating units derived from at least one polymerizable photosensitizer comprising repeating units derived from the at least the polymerizable photosensitizer comprising at least one polymerizable compound substituted with a polynuclear aromatic group, and
 wherein the polynuclear aromatic group absorbs light having a wavelength ranging from 300 nm and 600 nm.

DETAILED DESCRIPTION OF THE INVENTION

The present invention relates to a method for increasing the rate of a cationic photopolymerization. The method includes combining a photosensitizing composition, at least one, that is, one or more, cationic photoinitiator, and a cationically photopolymerizable composition; and exposing the combination to light. Light having a wavelength of 170 to 700 nm is typically effective in polymerizing the composition.

The photosensitizing composition component of the cationically polymerizable system of the present invention may be:
 at least one polymerizable photosensitizer;
 at least one polymeric photosensitizer, comprising repeating units derived from the photopolymerizable photosensitizer;
 at least one siloxane comprising repeating units derived from a hydrosilation reaction between an SH-containing siloxane and at least one vinyl or allyl compound substituted with a polynuclear aromatic group; or
 combinations thereof.

The polymerizable photosensitizer may be at least one polymerizable compound substituted with a polynuclear aromatic group which is capable of absorbing light having a wavelength ranging from 300 nm and 600 nm. The polynuclear aromatic group may be a residue derived from, for example, anthracene, naphthalene, perylene, pyrene, fluorene, carbazole, indole, benzocarbazole, acridone, phenothiazine, or thianthrene. In particular, the group may be a carbazole. Where the photosensitizer composition is a polymerizable photosensitizer, it may be desirable to use one substituted with a polynuclear aromatic group which is soluble in the mixture of photosensitizer, photoinitator and monomer(s). Many polynuclear aromatic compounds are insoluble in organic solvent systems. Where the photosensitizer composition is a polymeric photosensitizer, solubility of a copolymer having polynuclear aromatic substituents is typically improved over the polynuclear aromatic compound by copolymerization with soluble monomer(s).

The polynuclear aromatic-substituted polymerizable compound may be, for example, one or more ethylenically unsaturated monomers, epoxides, or oxetanes. In particular, an ethylenically unsaturated monomer may be used, including vinyl, allyl, acrylates, methcrylates, vinyl ethers and 1-propenyl ethers. The polymeric photosensitizer may additionally include repeating units derived from at least one vinyl comonomer, in particular, styrene, diethylfumarate, alkyl acrylate esters and/or alkyl methacrylate esters.

Of these polymerizable compounds, vinyl, allyl, acrylate and methacrylate substituents or groups may be polymerized using a radical, cationic and/or an anionic process. Strained heterocyclic rings, for example, epoxides or oxetanes, may be polymerized by a cationic or an anionic process. It should be noted that the polymeric photosensitizers may contain repeating units derived from epoxide, oxetane, acrylate or methacrylate groups, in addition to vinyl or allyl groups in contrast to repeating units of the siloxanes, which are derived from vinyl or allyl compounds having polynuclear aromatic substituents.

The polymeric photosensitizers may be derived from polymerization or copolymerization of one or more of the following:

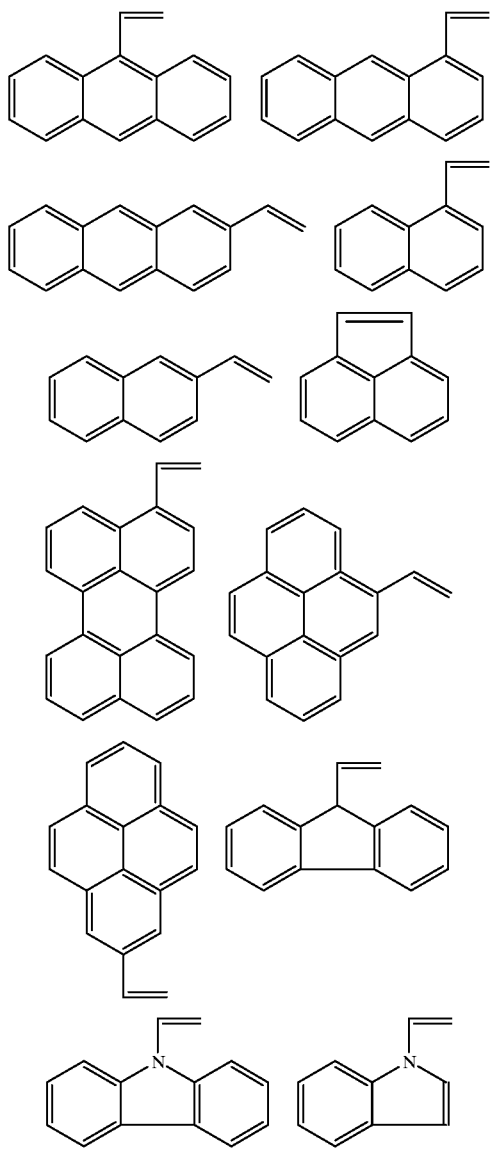

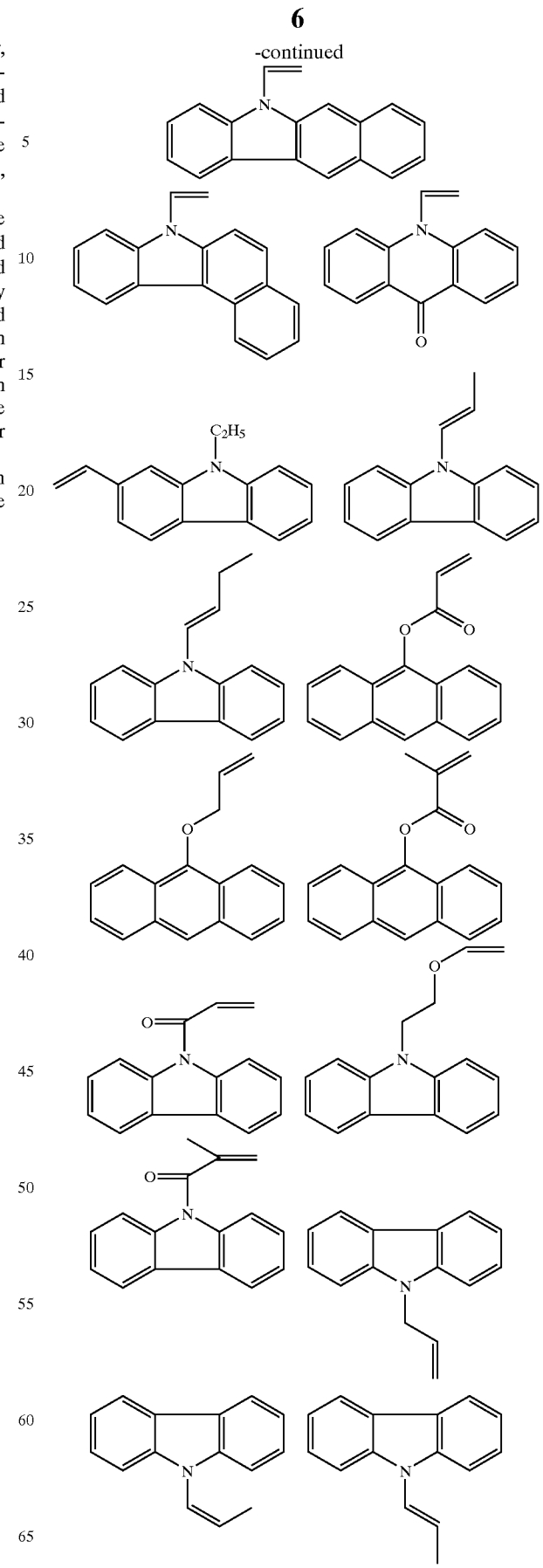

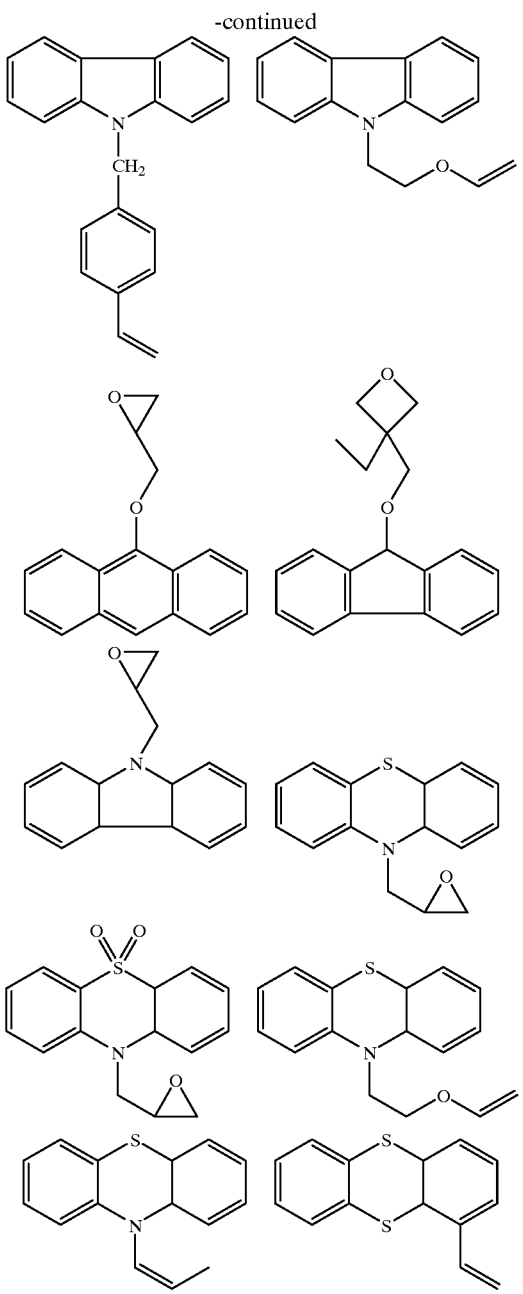

The cationic photoinitiator component of the cationically polymerizable system of the present invention comprises an onium salt, such as diaryliodonium salts, I, triarylsulfonium salts, II, and dialkylphenacylsulfonium salts, III. As noted above, three types of photoinitiators can efficiently initiate cationic photopolymerization when irradiation is carried out using short wavelength UV light. With the compositions of the present invention, the effective wavelength region is significantly expanded to the range 170 nm to 700 nm. In particular, the cationic photoinitiator may be (4-n-decyloxyphenyl)phenyliodonium hexafluoroantimonate (IOC10), (4-n-decyloxyphenyl)diphenylsulfonium hexafluoroantimonate (SOC10), S-dodecyl-S-methyl-S-phenacylsulfonium hexafluoroantimonate (DPS-$C_1C_{12}$) or a combination thereof.

The cationically photopolymerizable composition component of the cationically polymerizable system of the present invention may include any monomers or oligomers containing substituents that are capable of polymerizing using a cationic photoinitiator, or a combination of these monomers or oligomers. In particular, it may include an epoxide, an oxetane, a vinyl ether, a 1-propenyl ether or a combination of these. For example, it may include an epoxide such as 4-vinylcyclohexene dioxide (UCDO), limonene dioxide (LDO), cyclohexene oxide (CHO), 3,4-epoxycyclohexylmethyl 3-,4-epoxycyclohexanecarboxylate (ERL), bis-2(3,4-epoxycyclohexylethyl)-1,3(PC 1000), bis-(3,4-epoxycyclohexyl) adipate, epoxy silicone resins, glycidyl phenyl ether (GPE), dicyclopentadiene dioxide, bisphenol-A diglycidyl ether, bisphenol-F diglycidyl ether, 1,4-butanediol diglycidyl ether, diglycidyl ethers of tetrabromo-bisphenol-A, epoxy cresol novolacs, epoxy phenol novolacs, and diglycidyl phthalate, and combinations thereof. Specifically, the epoxide may be 4-vinylcyclohexene dioxide, limonene dioxide, cyclohexene oxide, 3,4-epoxycyclohexylmethyl 3-,4-epoxycyclohexanecarboxylate, bis-2(3,4-epoxycyclohexylethyl)-1,3-tetramethyldisiloxane, and combinations thereof. The cationically polymerizable composition may also include 2-chloroethylvinyl ether.

EXAMPLES

Examples 1–10, 17–25, and 38–43

General Procedure for Epoxy Photopolymerizations

Photopolymerizations were carried out at room temperature in solutions of the monomers containing various concentrations of the indicated photoinitiator. Concentrations used are given in units of mol % with respect to the epoxide monomer. The monomer/photoinitiator solutions were sandwiched between two 12–13 µm layers of an oriented and corona treated polypropylene film (General Electric Capacitor Dept., Hudson Falls, N.Y.), and then mounted in 5 cm×5 cm slide frames. The thickness of the liquid monomer films was estimated at 10–25 µm. Kinetic studies of the photopolymerizations of all the monomers were monitored using real-time infrared spectroscopy (RTIR). A Midac M-1300 FTIR spectrometer (Midac Corp., Irvine, Calif.) equipped with a liquid nitrogen cooled MCT detector was used. The instrument was fitted with a UVEXS Model SCU-110 mercury arc lamp (Sunnyvale, Calif.) equipped with a flexible liquid optic wand. The end of this wand was placed at a distance of 5 cm and directed at an incident angle of 45° onto the sample window. UV light intensities were measured with the aid of a UV Process Supply, Inc. radiometer (Chicago, Ill.) at the sample window. Infrared spectra were collected at a rate of 0.5–3 spectra per second using LabCalc, data acquisition software obtained from the Galactic Industries Corp. (Salem, N.H.) and were processed using GRAMS-386 software from the same company. The progress of the polymerizations was monitored by following the decrease of the IR absorbance due to either the vinyl ether double bonds centered at 1610 $cm^{-1}$, the 1-propenyl groups at 1661–1669 $cm^{-1}$ or the epoxy groups between 790–915 $cm^{-1}$ of the monomers were monitored. In all cases, three to five runs were recorded and the results averaged. Data reduction and subsequent conversion versus time plots were obtained using KaleidaGraph (Synergy Software, Reading, Pa.) software or Excel (Microsoft Corp., Redmond, Wash.) software.

Table 1 summarizes process variables for all photopolymerizations.

TABLE 1

Summary of Process Variables for Photopolymerizations
Using Polymerizable or High Molecular Weight Photosensitizers

| Ex. No. | Monomer Composition | Photosensitizer Composition* | Mol %, on monomer | Photoinitiator Composition | Mol %, on monomer | Light intensity, mJ/cm$^2$min |
|---|---|---|---|---|---|---|
| 1 | VCDO | none | — | IOC10 | 0.05 | 131 |
|   |      | PVK  | 0.1 |       |      |     |
| 2 | LDO  | none | — | IOC10 | 0.05 | 169 |
|   |      | NVK  | 2.0 |       |      |     |
| 3 | LDO  | none | — | DPS-C$_1$C$_{12}$ | 0.05 | 265 |
|   |      | NVK  | 2.0 |       |      |     |
| 4 | GPE  | none | — | IOC10 | 1 | 289 |
|   |      | NVK  | 40 |       |      |     |
| 5 | VCDO | none | — | IOC10 | 1 |  |
| 6 | VCDO | PVK  | 0.5 | IOC10 | 1 |  |
| 7 | VCDO | none | — | SOC10 | 1 |  |
| 8 | VCDO | PVK  | 0.5 | SOC10 | 1 |  |
| 9 | VCDO | none | — | DPS-C$_1$C$_{12}$ | 1 |  |
| 10 | VCDO | PVK | 0.5 | DPS-C$_1$C$_{12}$ | 1 |  |
| 17 | VCDO | none | — | IOC10 | 0.05 | 131 |
|    |      | PVK  |     |       |      |     |
| 18 | LDO  | none | — | SOC10 | 0.05 | 265 |
|    |      | NVK  |     |       |      |     |
| 19 | LDO  | none | — | DPS-C$_1$C$_{12}$ | 0.05 | 265 |
|    |      | NVK  |     |       |      |     |
| 20 | LDO  | NVK  | 2 | IOC10 | 0.05 | 145 |
|    |      | PVK  | 2 |       |      |     |
| 21 | CHO  | none | — | IOC10 | 0.5 | 103 |
|    |      | NVK  | 0.03 |     |      |     |
|    |      | PVK  | 0.03 |     |      |     |
| 22 | ERL  | NEK  | 1 | DPS-C$_1$C$_{12}$ | 1 | 2200 |
|    |      | 47 NVK/53 DEF | 1 |   |   |   |
|    |      | 50 NVK/50 DEF | 1 |   |   |   |
|    |      | 49 NVK/51 DEF | 1 |   |   |   |
| 23 | VCDO | PVK  | 0.1 | IOCIO | 0.05 | 228 |
|    |      | 47 NVK/53 DEF | 0.1 |   |   |   |
| 24 | 2-chloro ethyl vinyl ether | none | — | SOC10 | 1 | 245 |
|    |      | 47 NVK/53 DEF | 0.5 |   |   |   |
| 25 | PC-1000 | none | — | IOC10 | 0.5 | 405 |
|    |      | IV   | 1 |   |   |   |
|    |      | NEK  | 1 |   |   |   |
| 38 | LDO  | none | — | IOC10 | 0.1 | 378 |
|    |      | VIB  | 2 |   |   |   |
|    |      | VII(POLY VI) | 2 |   |   |   |
| 39 | CHO  | none | — | IOC10 | 1 | 200 |
|    |      | VIII | 1 |   |   |   |
|    |      | X(POLY VIII) | 1 |   |   |   |
| 40 | CHO  | none | — | SOC10 | 1 | 200 |
|    |      | VIII | 0.5 |   |   |   |
|    |      | X(POLY VIII) | 0.5 |   |   |   |
| 41 | CHO  | none | — | DPS-C$_1$C$_{12}$ | 1 | 200 |
|    |      | IX(POLY VIII) | 1 |   |   |   |
| 42 | CHO  | none | — | IOC10 | 1 | 200 |
|    |      | X    | 1 |   |   |   |
|    |      | XI(POLY XI) | 1 |   |   |   |
| 43 | 2-chloro ethyl vinyl ether | none | — | IOC10 | 0.2 | 200 |
|    |      | X    | 0.5 |   |   |   |

*Compositions: see relevant Example No. for chemical name/structure of numbered composition

Example 1

Figure 1:
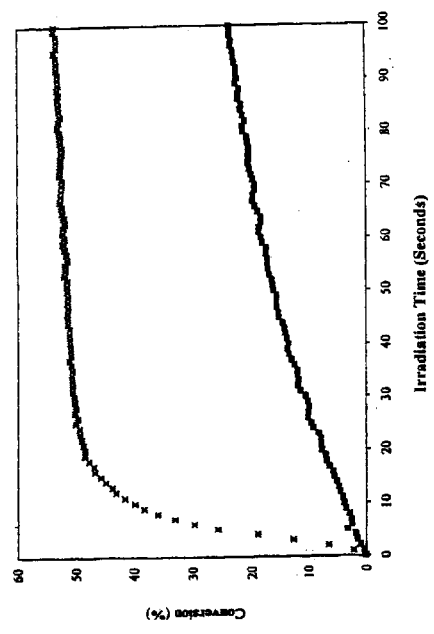
FIG. 1 shows FT-RTIR curves comparing the polymerization of 4-vinylcyclohexene dioxide (VCHO) alone (■) and in the presence of 0.1% polyvinylcarbazole (PVK) (*). (Light intensity 131 mJ/cm$^2$ min; 0.05% IOC10)

4-Vinylcyclohexene dioxide was photopolymerized, alone and in the presence of PVK using IOC10 photoinitiator, and the procedure shown above. The RTIR curves for the photopolymerization are shown in FIG. 1. The much higher rate of polymerization for the PVK photosensitized polymerization is indicative of efficient photosensitization of the photoinitiator.

Examples 2 and 3

Figure 3:
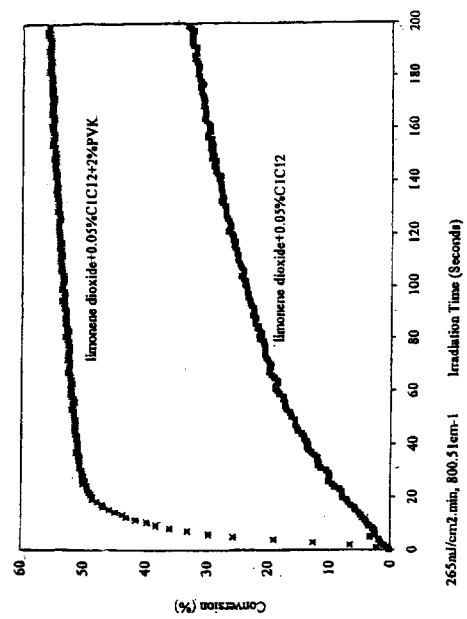
FIG. 3 is a comparison between the epoxide polymerization of limonene dioxide alone (■) and in the presence of 2.0% NVK (*). (Light intensity 265 mJ/cm$^2$ min, 0.05% DPS-$C_1C_{12}$).

The use of PVK as a photosensitizer for SOC10 and DPS-C$_1$C$_{12}$ in the polymerization of limonene dioxide is shown in FIGS. 2 and 3, respectively. In both cases dramatic acceleration of the polymerization took place in the presence of PVK.

Example 4

Figure 4:
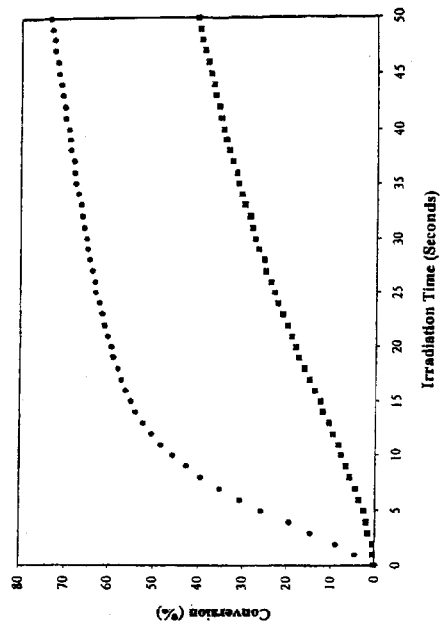
FIG. 4 is a comparison between the epoxide polymerization of glycidyl phenyl ether (GPE) alone (■) and in the presence of 40% NVK (●). (Light intensity 289 mJ/cm$^2$ min; 1.0% IOC10)

Gycidyl phenyl ether was photopolymerized in the presence and absence of 40% NVK. The kinetic curves are shown in FIG. 4. A marked acceleration of the rate of polymerization of the epoxide was noted in the presence of NVK.

Example 5–10

UV cure studies of the polymerization of 4-vinylcyclohexene dioxide were conducted using 1% of three different cationic photoinitiators, IOC10, SOC10 and DPS-$C_1C_{12}$. The polymerizations were carried out using a three-hundred W GE H-3T7 mercury arch lamp equipped with a manual shutter. The distance of the lamp was fixed at 10 cm. The minimal time to produce a tack free 50 μm film was recorded as the tack free time. The results are shown in Table 2. In all cases the tack free time was reduced in the presence of PVK.

TABLE 2

PVK Photosensitized UV Cure of 4-Vinylcyclohexene Dioxide

| Experiment No. | Photoinitiator | Conc. PVK (%) | Tack-free time (sec) |
|---|---|---|---|
| 5 | IOC10 | — | 6 |
| 6 | IOC10 | 0.5 | 4 |
| 7 | SOC10 | — | 8 |
| 8 | SOC10 | 0.5 | 6 |
| 9 | DPS-$C_1C_{12}$ | — | 7 |
| 10 | DPS-$C_1C_{12}$ | 0.5 | 6 |

Examples 11–15

Synthesis of NVK—Diethylfumarate Copolymers

The following procedure is typical for that employed for the synthesis of the NVK/DEF copolymers prepared. Compositions of the copolymers, yield and molecular weights of the copolymers produced are shown in Table 3.

NVK (2.24 g, 0.0116 mole) was dissolved in diethylfumarate (2.00 g, 0.0116 mole) in a clean, dry glass vial, 2,2-azobisisobutyronitrile (0.076 g, 0.00046 mole) added and the mixture purged with nitrogen and sealed. The mixture placed in an ultrasonic water bath at 25–35° C. to dissolve the initiator. The resulting pale yellow solution was placed in an oil bath at 78° C. After 5–10 minutes under nitrogen, a foamed solid polymer formed. The polymer was dissolved in chloroform and precipitated in methanol. After drying in a vacuum oven at 50° C., 2.2 g of a white polymer powder was obtained. GPC measurement of the molecular weight gave a $M_W$=42400 g/mol and a $M_W/M_N$=4.4.

TABLE 3

Copolymerization* of NVK with Diethylfumarate or Butyl Acrylate

| Ex. No. | Monomer | % CTA | $M_W$ (g/mol) | MWD | Yield (%) | Vol. % NVK | Wt. % NVK |
|---|---|---|---|---|---|---|---|
| 11 | DEF | — | 42400 | 4.4 | 52 | 47 | 50 |
| 12 | DEF | 2.0 | 11500 | 3.8 | 65 | 50 | 53 |
| 13 | DEF | 4.0 | 9200 | 2.2 | 71 | 49 | 51 |
| 14 | BA | 2.0 | 17000 | 5.0 | 69 | 44 | 54 |
| 15 | BA | 4.0 | 10000 | 3.8 | 67 | 43 | 53 |

*Equimolar mixture of NVK with the indicated monomer using 2% 2,2'-azobisisobutyronitrile.

NVK polymerizes with these two monomers to give largely alternating polymers. In the absence of a chain transfer agent, copolymerization with DEF gave olecular weight of 42400 g/mol (Example 11). Copolymerizations were also carried out in the presence of lauryl mercaptan as a free radical chain transfer agent (CTA) in order to lower molecular weight copolymers were obtained. Table 4 shows the solubility of PVK as compared to the NVK copolymers in three different difunctional epoxide monomers. It can be seen that PVK was soluble only in LDO. The silicone diepoxide, PC-1000, was a very poor solvent for PVK and all the NVK copolymers. Good solubility was displayed by the copolymers in LDO and ERL.

TABLE 4

Solubility Characteristics of PVK Copolymers

| Polymer | PVK | Cop.-1 | Cop.-2 | Cop.-3 | Cop. 4 | Cop-5 |
|---|---|---|---|---|---|---|
| $M_w$ (g/mol) | 256700 | 42400 | 11500 | 9200 | 17000 | 10000 |
| Solubility* | | | | | | |
| PC1000 | ns | ns | ns | ns | ns | ns |
| LDO | s | s | s | s | s | s |
| ERL | ns | s | s | s | s | ns |

Example 16

Preparation of 1,3-Bis-(2-carbazolyethyl)-1,1,3,3-tetramethyldisiloxane (IV)

A dimeric carbazole photosensitizer was synthesized as shown below by the hydrosilation of NVK with 1,1,3,3-tetramethyldisiloxane. Hydrosilation proceeded smoothly in the presence of polymer-bound Wilkinson's catalyst to give the desired hydrosilation dimer IV in 51% yield as a colorless powder.

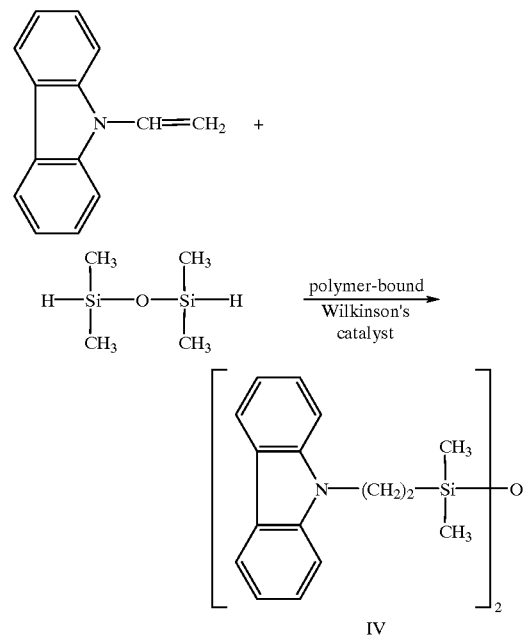

IV

Into a 25 mL round bottom flask equipped with a magnetic stirrer and reflux condenser were placed 5.1 g (0.026 mol) of N-vinyl carbazole, 10 mL of toluene that was freshly distilled from sodium metal, 1.8 g (0.013 mol) of 1,1,3,3-tetramethyldisiloxane and 3 mg of polymer-bound Wilkinson's catalyst. The reaction mixture was heated to 80° C. and maintained at that temperature for 24 hours. During reaction, the reaction mixture became increasingly more viscous as reaction proceeded. Upon cooling to room temperature, the product solidified. The crude product was purified by dissolving it in a small amount of THF and slowly adding the resulting solution to cold methanol. The product, IV, was obtained as a colorless powder and was recovered by filtration. After drying under vacuum, there were obtained 3.5 g (51% yield) of pure IV. $^1$H-NMR spectroscopy confirmed the structure of this compound. It is interesting to note that S—H addition takes place to the vinyl double bond such that the silicon becomes bonded to the terminal carbon of the double bond. There is no evidence in the spectrum of methyl bands arising from the reverse addition to the vinyl double bond. In agreement with this structure, the $^{29}$Si-NMR spectrum shows only a single resonance located at 7.00 ppm.

$^1$H-NMR spectrum in CDCl$_3$ δ (ppm) H$_a$, s, 0.24; H$_b$, m, 1.3; H$_c$, m, 4.4; H$_d$, d, 8.1; H$_{e,f,g}$, m, 7.2–7.5.

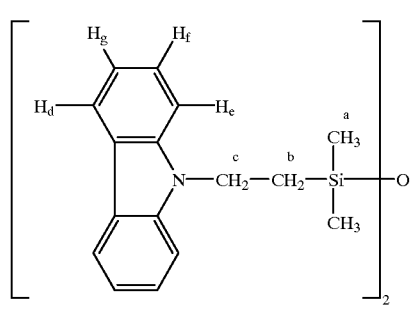

IV

Example 17

Figure 5:
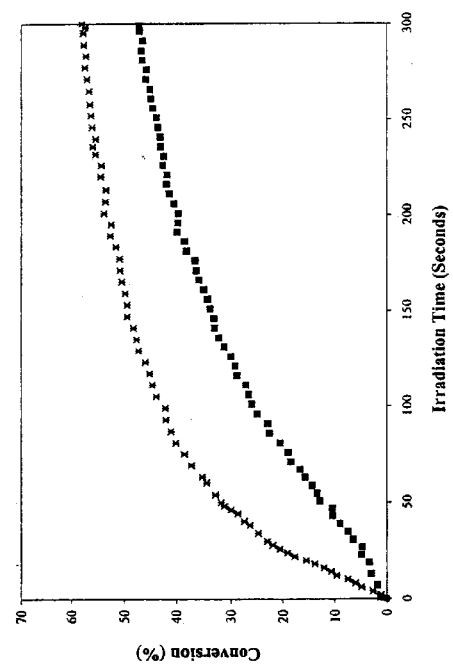
FIG. 5 is an FT-RTIR comparison of the polymerization of 4-vinylcyclohexene dioxide alone (■) and in the presence of 0.1% PVK (*). (Light intensity 131 mJ/cm$^2$ min; 0.05% IOC10)

VCDO was polymerized with IOC10 as the photoinitiator using broadband UV light in the presence and absence of PVK. The kinetic curve is shown in FIG. 5. It can be seen that there is a dramatic increase in the rate of polymerization in the presence of the polymeric photosensitizer, and there is no induction period. This suggests that PVK is sufficiently nonbasic that competition with the VCDO monomer for initiating protons and propagating oxonium cations does not appear to occur.

Examples 18 and 19

Figure 6:
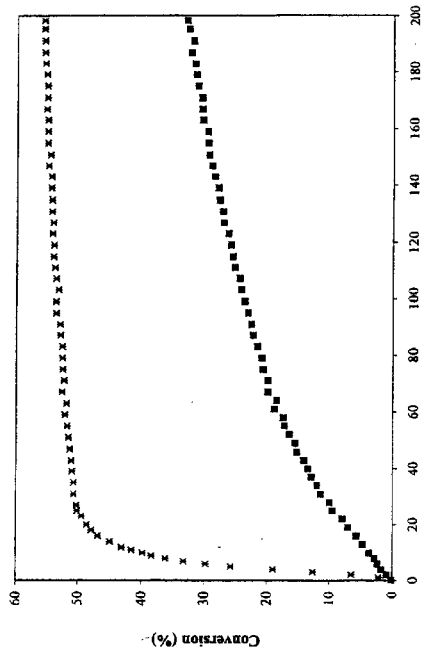
FIG. 6 is an FT-RTIR comparison of the polymerization of limonene dioxide alone (■) and in the presence of 2.0% PVK (*). (Light intensity 265 mJ/cm$^2$ min; 0.05% SOC10)
Figure 7:
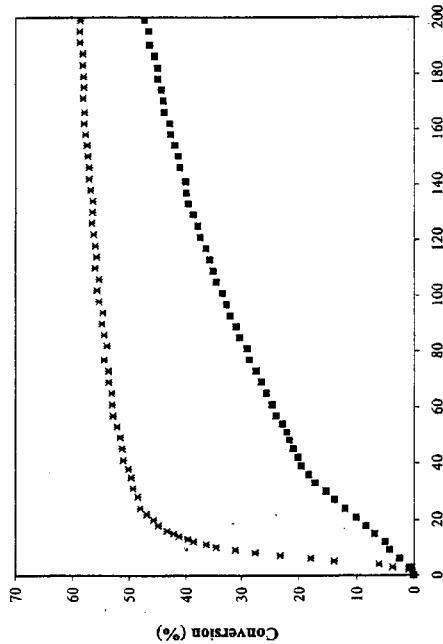
FIG. 7 is a comparison of the polymerization of limonene dioxide by FT-RTIR alone (■) and in the presence of 2.0% PVK (*). (Light intensity 265 mJ/cm$^2$ min; 0.05% DPS-$C_1C_{12}$ $SbF_6^-$)

Limonene dioxide was photopolymerized using PVK as a photosensitizer, and SOC10 or DPS C$_1$C$_{12}$. SbF$_6$ as photoinitiators. For comparison, the polymerization was also conducted in the absence of PVK. The kinetic curves are shown in FIGS. 6 and 7. As noted above, dramatic acceleration of the polymerizations took place in the presence of PVK as a result of photosensitization for both of these two different types of sulfonium salts. This implies that the photoexcited PVK is capable of reducing onium salts with very different reduction potentials.

Examples 20–21

Antenna Effects in Photosensitization by PVK

Figure 8:
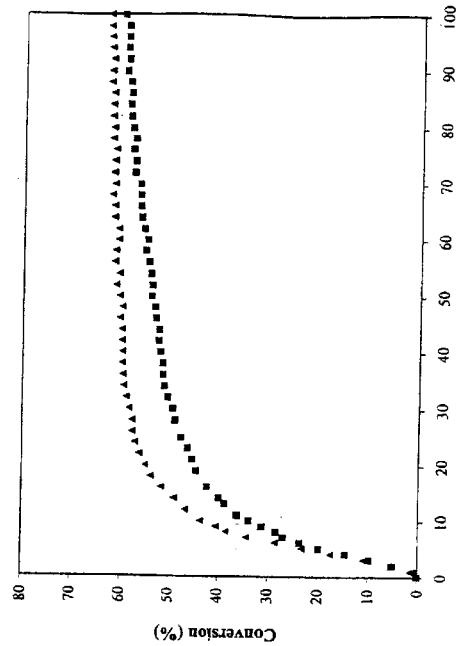
FIG. 8 is an FT-RTIR comparison of the polymerization of limonene dioxide in the presence of 2.0% NVK (■) and PVK (▲). (Light intensity 145 mJ/cm$^2$ min; 0.05% SOC10)

In order to determine whether PVK exhibits any special photosensitization properties for onium salt induced cationic photopolymerizations that would make it more efficient than related monomolecular carbazole compounds, two brief studies were undertaken. In FIG. 8 is shown a study in which two polymerizations of LDO using IOC10 were carried out comparing NVK and PVK as photosensitizers. Identical molar quantities (2.0 mol % based on the monomer) of carbazole moieties were used in each experiment. Calculations of the initial slopes of the two conversion versus time curves gives 3.5 for PVK and 2.6 for NVK. These results indicate that under the same experimental conditions, both the monomolecular and polymeric photosensitizers have very similar efficiencies of photosensitization. Analogous results were observed when PVK is compared to N-ethylcarbazole (NEK) or N-methylcarbazole. These results suggest that both monomolecular and polymeric photosensitizers behave similarly.

Figure 9:
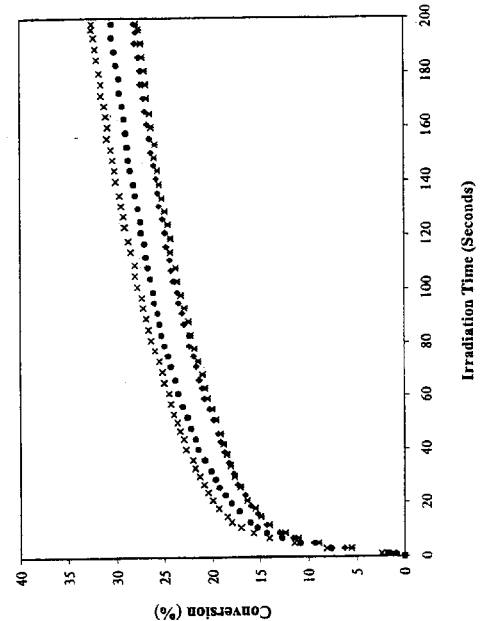
FIG. 9 is an FT-RTIR study of the photopolymerization of cyclohexene oxide (CHO) in the presence of 0.5% IOC10 alone (●) and using 0.2% PVK (X) and 0.2% NEK (▲). (Light intensity 103 mJ/cm$^2$ min)

To either confirm or exclude the existence of an "antenna effect" the rates of polymerization of a monomer in the presence of various concentrations of PVK and a monomolecular photosensitizer were carried out. If intramolecular energy transfer takes place along the chain of PVK, it should be effective in channeling that energy to sensitize the photolysis of an onium salt remote from the site of excitation. This would be reflected in a higher rate of polymerization for PVK as compared to a monomolecular photosensitizer. This effect should be most readily observable at low photosensitizer/onium salt concentrations. FIG. 9 gives the results of an investigation of the photopolymerization of cyclohexene oxide (CHO) in with 0.5% IOC10 using 0.03% of both NEK and PVK. A curve in which no photosensitizer was present is included for comparison. Again, little difference was observed between the initial rates of polymerization using these two photosensitizers. This leads to the conclusion that intramolecular energy transfer in PVK in a monomer solution is most likely very inefficient and, thus, each repeat unit along the chain behaves as an independent photosensitizer entity.

While PVK does not exhibit an "antenna effect" that would enhance its activity as a photosensitizer, it also does not display other reported effects that could significantly detract from its efficiency, such as excimer emission (fluorescence) or phosphorescence resulting from interaction respectively, of the presence of singlet and triplet excitons in the photoexcited polymer. These emissions represent energy-wasting, excited state deactivation processes that can reduce the efficiency of photosensitization.

Example 22–24

Copolymers of NVK as Photosensitizers

Figure 10:
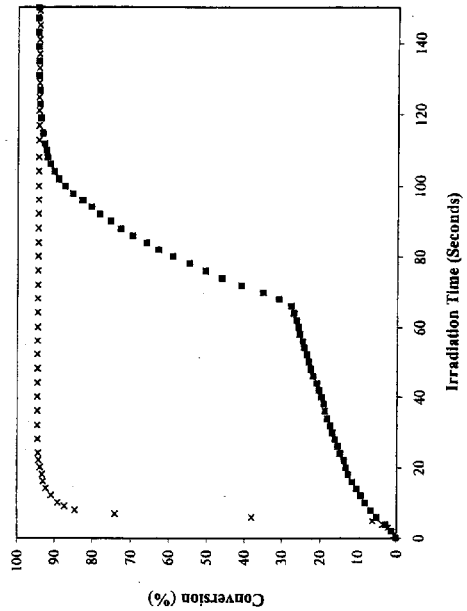
FIG. 10 is an FT-RTIR comparison of the photosensitized polymerization of 3,4-epoxycyclohexylmethyl 3',4'-epoxycyclohexane-carboxylate (ERL) in the presence of copopolymers of Example 11, (X); 2, (*); and 4 (♦)(1.0% carbazole repeat units) and with 1.0% NEK (●) using 1.0% DPS-$C_1C_{12}$ $PF_6$ as the photoinitiator. (Light intensity 2200 mJ/cm$^2$ min)
Figure 11:
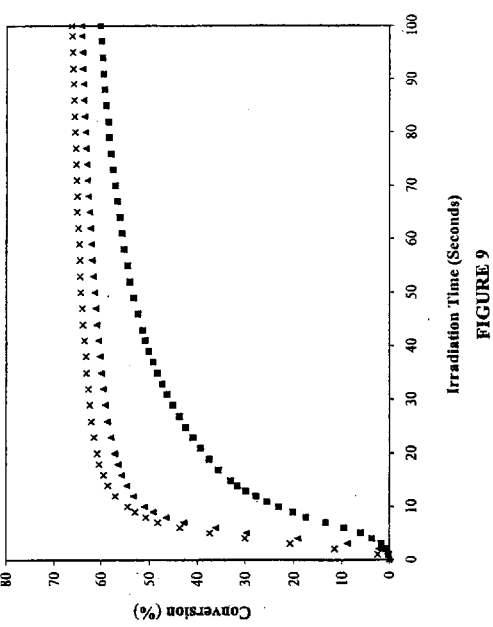
FIG. 11 is an FT-RTIR study of the photosensitized polymerization of VCDO carried out with the copolymer of Example 12 (X) and PVK (▲) using equimolar (0.1%) amounts of carbazole repeat units and with 0.05% IOC10 as the photoinitiator. (Light intensity 228 mJ/cm$^2$ min)

FIG. 10 shows a comparison of the photosensitization of the ring-opening epoxide polymerizations of ERL in the presence of three NVK copolymers (Examples 11, 12, 14) and with NEK using 1.0% DPS-C$_1$C$_{12}$ PF$_6$ as the photoinitiator. In each case, equivalent amounts (0.1%) of carbazole groups were used. The results show that the copolymers display essentially the same level of efficiency of photosensitization as NEK in this photopolymerization. In FIG. 11 are compared the photosensitized polymerizations of VCDO using 0.1% of the copolymer of Example 12 and PVK. Again, this comparison was made using identical molar amounts of carbazole repeat units. The nearly identical results for the two polymeric photosensitizers once again confirm that the carbazole units behave essentially as independent photosensitizing chromophors.

Figure 12:
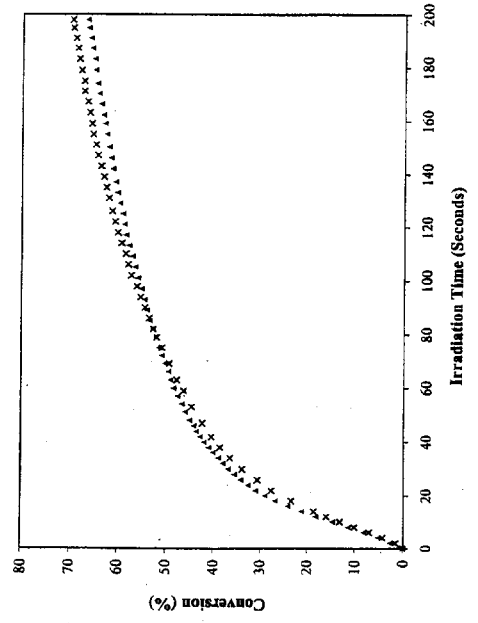
FIG. 12 is an FT-RTIR study of the photopolymerization of 2-chloroethyl vinyl ether alone (■) and in the presence of the PVK/DEF copolymer of Example 11 (X), at the 0.5% level. (Light intensity 245 mJ/cm$^2$ min; 1.0% SOC10)

FIG. 12 shows the results of a study in which the copolymer of Example 11 was used to photosensitize the polymerization of 2-chloroethyl vinyl ether in the presence of 1.0% SOC10 as a photoinitiator. Copolymers of NVK with DEF displayed excellent solubility in this monomers. Marked improvement of the photoresponse of the copolymer photosensitized polymerization using broadband UV light was observed as compared to the parallel polymerization carried out in the absence of a photosensitizer. Direct comparison of copolymer of Example 11 with NVK shows that both exhibit identical levels photosensitization activity in the polymerization of this monomer when compared on the basis of the same molar equivalents of carbazole groups.

Example 25

Dimeric Photosensitizer

Figure 13:
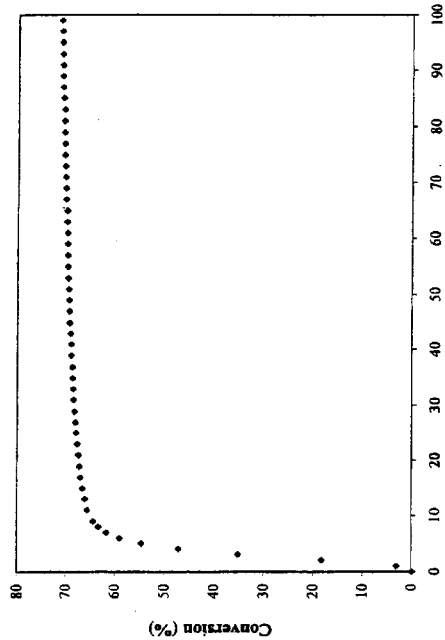
FIG. 13 is a study of the photosensitized polymerization of PC-1000 by FT-RTIR with 0.5% IOC10 alone (●) and in the presence of 1.0% IV, (X) and NEK, (▲) as photosensitizers. (Light intensity 405 mJ/cm$^2$ min)

Dimer IV, prepared according to the procedure of Example 16, was readily soluble in PC-1000. FIG. 13 shows the results of photopolymerizations comparing this photosensitizer with NEK. IV displayed excellent photosensitization activity that is very similar to NEK in this highly reactive monomer. These results suggest that a wide variety of other oligomeric and polymeric carbazole photosensitizers can be prepared by the hydrosilation of NVK with the appropriate Si—H functionalized substrates.

Example 26

Preparation of 9-Allyl carbazole (V)

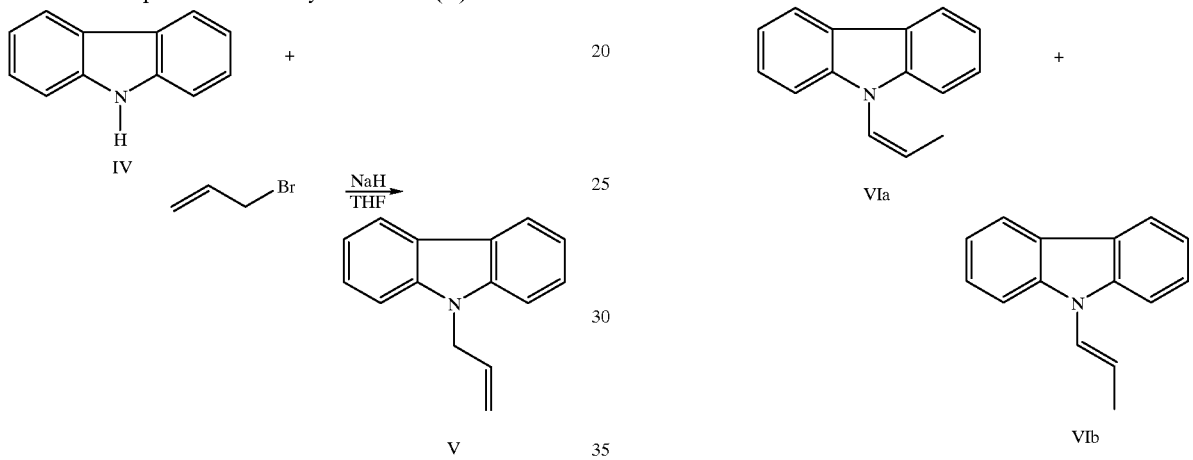

Into a 500 mL round bottom flask fitted with a mechanical stirrer, addition funnel, reflux condenser and nitrogen inlet were placed 12 g of sodium hydride (60% dispersion in mineral oil) and 30 mL of THF. Carbazole (33.4 g, 0.2 mole) was dissolved in 200 mL THF and the pale yellow solution was added dropwise to the reaction mixture while stirring and maintaining the temperature at 35–40° C. Thereafter, 36.2 g (0.3 mole) of allyl bromide was added drop wise to the reaction mixture and stirring continued for an additional 15 minutes. Tetra-n-butyl ammonium bromide (1.3 g) was added followed by stirring for 20 minutes, and then the temperature was raised to 65° C. and kept at that temperature overnight. The reaction mixture was cooled to room temperature and after filtration, the solvent was removed using a rotary evaporator. The resulting yellow solid was twice recrystallized from methanol to give 34 g (81% yield) of colorless crystalline 9-allyl carbazole m.p. 53–54° C.

Example 27

Preparation of cis- and trans-9-(1-Propenyl) carbazole (VIa and VIb)

Method A: Base-Catalyzed Isomerization

Into a 100 mL round bottom flask fitted with a magnetic stirrer, reflux condenser and nitrogen inlet were placed 2.07 g (0.01 mole) of 9-allyl carbazole, 1.12 g (0.01 mole) of potassium t-butoxide and 10 mL of DMSO. The reaction mixture was stirred for 20 minutes at room temperature and then was heated to 120° C. and kept at that temperature for two hours. TLC on silica gel was used to monitor the reaction. After cooling to room temperature, the reaction mixture was poured into 20 mL of distilled water and extracted with ethyl ether. The organic layer was washed with distilled water to remove DMSO, then anhydrous sodium sulfate was added and the mixture stirred for an hour. Thereafter, the sodium sulfate was removed by filtration and a rotary evaporator was used to remove the solvent. 9-(1-Propenyl)carbazole was isolated in 63% yield (1.3 g) as a pale yellow viscous liquid. $^1$H NMR (300 MHz, CDCl$_3$) showed that the product was consisted of approximately a 1:2 ratio of cis and trans 9-(1-propenyl)carbazole isomers.

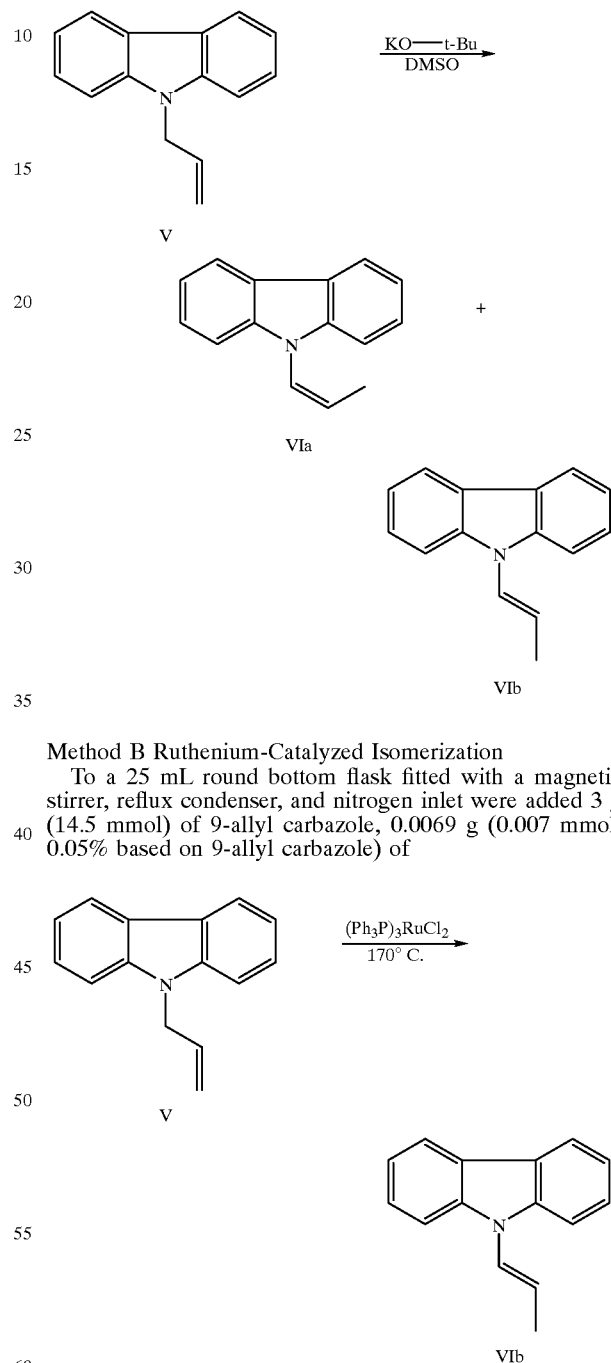

Method B Ruthenium-Catalyzed Isomerization

To a 25 mL round bottom flask fitted with a magnetic stirrer, reflux condenser, and nitrogen inlet were added 3 g (14.5 mmol) of 9-allyl carbazole, 0.0069 g (0.007 mmol, 0.05% based on 9-allyl carbazole) of tris(triphenylphosphine)ruthenium (II) dichloride. The reaction mixture was heated at 170° C. under nitrogen for 16 h. After cooling, approximately 15 mL of methanol and 1 g of alkaline decolorizing carbon (Norite-A) was added and the mixture and heated to reflux for half an hour. Then the mixture was filtered and the filtrate was kept in refrigerator for the product to crystallize. There were obtained 0.7 g (23% yield) colorless crystalline trans 9-(1-propenyl) carbazole m.p. 47–50° C.

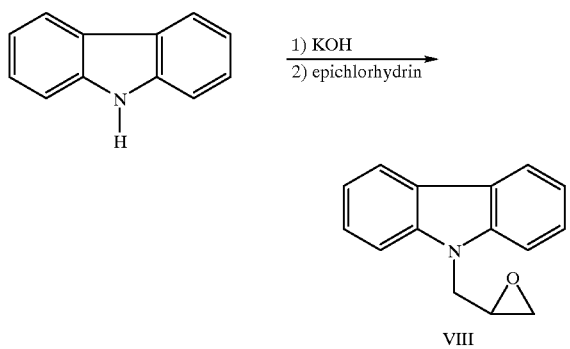

Example 28

Synthesis of 9-(2,3-Epoxypropyl)carbazole (N-Glycidylcarbazole, VIII)

The method of Inaki (Y. Inaki, G. Sheybani, K. *Takemoto, Technol. Rep. Osaka Unv.* 1975,25, 249; *Chem. Abstr.* 1975, 83, 59374s) was employed for the synthesis of VIII. A yield of 34% VIII with a m.p. of 110–111° C. (lit. m.p. 110–111° C.) was obtained after two recrystallizations from ethanol.

Example 29

Preparation of 9-(2-Vinyloxyethyl)carbazole (2-(9-Carbazolyl)ethyl vinyl ether) IX Combined into a 500 mL round bottom flask fitted with a magnetic stirrer, reflux condenser and nitrogen inlet were 16.7 g (0.1 mol) of carbazole, 15 mL (0.15 mol) of 2-chloroethyl vinyl ether and 250 mL of THF. The reaction mixture was stirred for 15 minutes at room temperature and then 6.72 g (0.12 mol) of KOH and 1.0 g $Na_2CO_3$ added and stirring continued for an additional 1 h. The reaction mixture was refluxed overnight, cooled and the solvent removed on a rotary evaporator. An oil was obtained which was washed with distilled water. Colorless crystals of IX m.p. 81–82° C. (lit. m.p. 78.5–79° C.) were obtained upon recrystallization from ethanol. The overall yield was 72%.

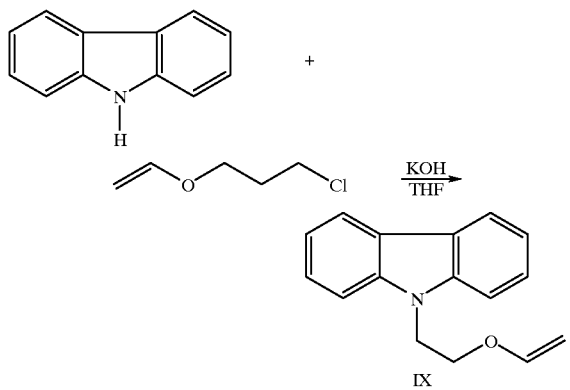

Examples 30–36

Polymerization of Carbazole Monomers VI, VIII and X

The experimental conditions and results obtained in the cationic polymerizations of the three carbazole monomers are summarized in Table 1.

Method A: Polymerization of 9-(1-Propenyl)carbazole

In a vial, 0.5 g of trans-9-(1-propenyl)carbazole and 0.013 g of IOC10 (2 mole % based on 9-(1-propenyl)carbazole) were dissolved in 1 mL of dichloromethane. The solution was exposed to UV light using a GE H3T-7 200 W medium pressure mercury arc lamp for 3 minutes and then poured into methanol. After filtering and drying the resulting precipitated oligomer in a vacuum oven, a yield of 0.25 g (50%) was obtained.

Method B

Photoinduced cationic polymerizations were carried out by dissolving 1.0 g of monomer and 0.5% of IOC10 in 5 mL of dry dichloromethane and placing the solutions in sealed 15 mm i.d. quartz reaction tubes. The samples were irradiated at 25° C. in a Rayonet photochemical reactor equipped with a merry-go-round sample holder and sixteen low-pressure mercury lamps with an emission wavelength 250 nm. After 10 min irradiation, sample tubes were withdrawn. The polymer solutions were poured into cold methanol and the resulting precipitated polymers isolated by filtration and dried overnight in a vacuum oven at 50° C.

Method C

Low temperature cationic polymerizations were carried out at the designated temperatures by injecting boron trifluoride etherate through a rubber septum into a flask containing a magnetic stirrer and 2.0 g of monomer dissolved in 15 mL dry dichloromethane. After stirring for 1 hour, the solution was poured into cold methanol and the precipitated polymer collected by filtration and dried overnight in a vacuum oven at 50° C.

Example 37

Figure 14:
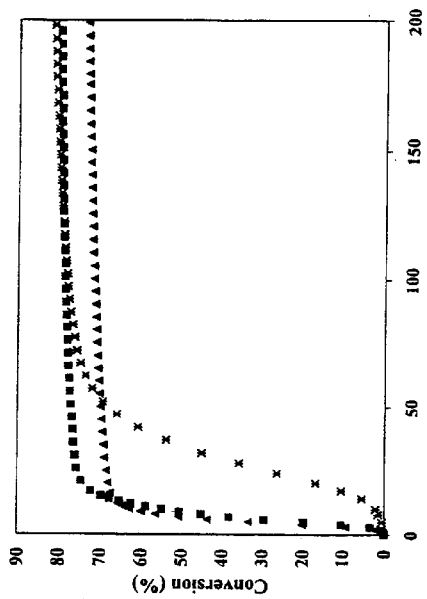
FIG. 14 is an FTIR study of the cationic photopolymerization of a 2:1 mixture of cis and trans-9-(1-propenyl) carbazole. (Light intensity 510 mJ/cm$^2$ min, 1.0% IOC10).

FIG. 14 shows the results of a RTIR study of the bulk cationic polymerization of a 1:2 mixture of cis and trans-9-(1-propenyl)carbazole carried out in the presence of 1.0% IOC10. Each isomer has a distinct and characteristic IR absorption band (cis, 1661 $cm^{-1}$; trans, 1669 $cm^{-1}$). In the study shown in FIG. 2, the curve is an average of the independent rates of both isomers. Due to the position and broadness of the two absorption bands, they could be accurately deconvoluted and integrated. It can, however, be seen, that the cationic photopolymerization rate of the trans isomer takes place more rapidly than the corresponding cis isomer. Overall, the cationic polymerizations of both 9(1-propenyl)carbazole isomers were very rapid.

Example 38

Figure 15:
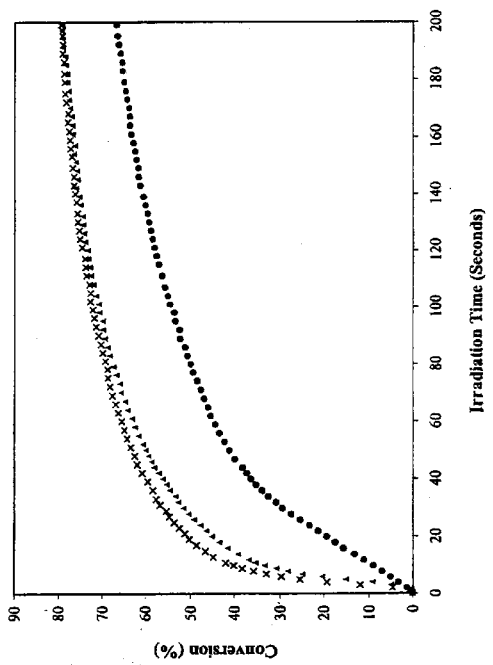
FIG. 15 is a comparison between the polymerization of limonene dioxide alone (■) and in the presence of 2.0% 9-(1-propenyl)carbazole. (*) and 2.0% poly[9-(1-propenyl) carbazole] (X). (Light intensity 378 mJ/cm$^2$ min; 0.1% IOC10)

FIG. 15 depicts the response of the polymerization of the limonene dioxide to photosensitization by 2.0% trans-9-(1-propenyl)carbazole (VIb). A curve for the polymerization of limonene dioxide in the absence of the photosensitizer is also provided for comparison. A marked enhancement of the rate of the polymerization of limonene dioxide was observed in the presence of the monomeric carbazole photo sensitizer.

Example 40

Trans-9-(1-propenyl)carbazole was polymerized by UV irradiation of a dichloromethane solution containing 1.0% IOC10. After isolation and purification of the oligomer VII by repeated dissolution and precipitation into methanol, VII was employed as a photosensitizer for the photopolymerization of limonene dioxide. These results are also shown in FIG. 15. Oligomer VII displays essentially the same photosensitization activity as its corresponding monomer in the polymerization of limonene dioxide.

Example 41

Figure 16:
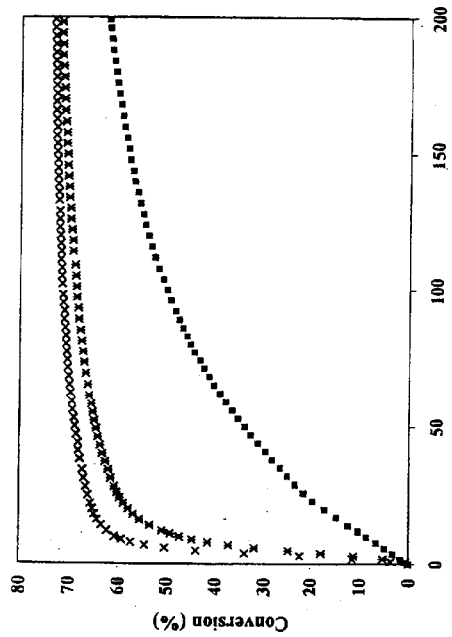
FIG. 16 is a comparison of the polymerization of cyclohexene oxide in the presence of 1.0% 9-(2,3-epoxypropyl) carbazole (▲) and poly[9-(2,3-epoxypropyl)carbazole] (■). Polymerization in the absence of a photosensitizer (*). (Light intensity 200 mJ/cm$^2$ min; 1.0% IOC10)

Compared in FIG. 16 are the photosensitized polymerizations of cyclohexene oxide with IOC10 as the photoinitiator using 9-(2,3-epoxypropyl)carbazole, VIII, and its polymer, IX, as photosensitizers. A curve for the polymerization of the monomer in the absence of a photosensitizer is also included. As can be noted from the higher initial slopes obtained for these photopolymerization, the effect of adding either of these photosensitizers was to substantially increase the rate of the photopolymerization. Very similar effects were observed for the analogous studies shown in FIGS. 17 and 18 in which respectively, sulfonium salt photoinitiators SOC10 and $C_1C_{12}$-DPS were employed as photoinitiators in the polymerization of cyclohexene oxide. Accordingly, it may be concluded that these carbazole photosensitizers can be effectively and conveniently employed for the photosensitization of a broad range of diaryliodonium, triarylsulfonium and dialkylphenacylsulfonium salt cationic photoinitiators.

Examples 42–43

A study of the photosensitized polymerization of cyclohexene oxide using 9-(2-vinyloxyethyl)carbazole, X, and its polymer, XI, is shown in FIG. 19. As before, both the carbazole monomer and polymer are effective photosensitizers for the photopolymerization of cyclohexene oxide. Interestingly, X was also an effective photosensitizer for the cationic vinyl polymerization of 2-chloroethyl vinyl ether at low concentrations. This is depicted in FIG. 20. A dramatic reduction in the induction period of the photopolymerization was observed in the presence of the photosensitizer. Facile incorporation of the photosensitizer into the polymer chain is expected in this case.

What is claimed:

1. A method for increasing the rate of a cationic photopolymerization, said method comprising:
   a. combining
      i. a photosensitizing composition selected from the group consisting of
         at least one polymeric photosensitizer comprising repeating units derived from at least one polymerizable compound comprising a polynuclear aromatic group capable of absorbing light having a wavelength ranging from 300 nm to 600 nm;
         at least one siloxane comprising repeating units derived from a hydrosilation reaction between a SH-containing siloxane and at least one vinyl or allyl compound substituted with a polynuclear aromatic group capable of absorbing light having a wavelength ranging from 300 nm to 600 nm;
         and combinations thereof; and
      ii. at least one cationic photoinitiator comprising an onium salt; and
      iii. a cationically photopolymerizable composition; and
   b. exposing the combination to light.

2. A method according to claim 1, wherein said photosensitizing composition comprises said polymeric photosensitizer.

3. A method according to claim 2, wherein said polymeric photosensitizer comprises repeating units derived from at least one polymerizable photosensitizer comprising at least one polymerizable compound substituted with said polynuclear aromatic group, and said polymerizable compound is selected from the group consisting of ethylenically unsaturated monomers, epoxides, oxetanes, and combinations thereof.

4. A method according to claim 3, wherein said polymerizable compound is at least one ethylenically unsaturated monomer.

5. A method according to claim 4, wherein said polymerizable compound is 9-vinylcarbazole.

6. A method according to claim 3, wherein said polymeric photosensitizer additionally comprises repeating units derived from at least one vinyl comonomer.

7. A method according to claim 6, wherein said vinyl comonomer is selected from the group consisting of styrene, diethylfumarate, alkyl acrylate esters and alkyl methacrylate esters.

8. A method according to claim 6, wherein said vinyl comonomer is diethylfumarate.

9. A method according to claim 6, wherein said vinyl comonomer is butyl acrylate.

10. A method according to claim 6, wherein said polymeric photo sensitizer is a copolymer of 9-vinylcarbazole and diethylfumarate.

11. A method according to claim 6, wherein said polymeric photosensitizer is a copolymer of 9-vinylcarbazole and butyl acrylate.

12. A method according to claim 2, wherein said polymeric photosensitizer consists essentially of repeating units derived from 9-vinylcarbazole.

13. A method according to claim 1, wherein said photosensitizing composition comprises said siloxane.

14. A method according to claim 13, wherein said siloxane comprises repeating units derived from a hydrosilation reaction between a SH-containing siloxane and 9-vinylcarbazole.

15. A method according to claim 13, wherein said siloxane comprises repeating units derived from a hydrosilation reaction between a SH-containing siloxane and at least one vinyl or allyl compound substituted with a carbazole group.

16. A method according to claim 15, wherein said siloxane comprises 1,3-bis-(2-carbazoloethyl)-1,1,3,3-tetramethyldisiloxane.

17. A method according to claim 1, wherein said onium salt is selected from the group consisting of triarylsulfonium salts, diaryliodonium salts, and dialkylphenacylsulfonium salts.

18. A method according to claim 17, wherein said onium salt is selected from the group consisting of (4-n-decyloxyphenyl)phenyliodonium hexafluoroantimonate, (4-n-decyloxyphenyl)diphenylsulfonium hexafluoroantimonate, and S-dodecyl-S-methyl-S-phenacylsulfonium hexafluoroantimonate.

19. A method according to claim 1, wherein said cationically photopolymerizable composition comprises an epoxide, an oxetane, a vinyl ether, a 1-propenyl ether or a combination thereof.

20. A method according to claim 19, wherein said cationically photopolymerizable composition comprises at least one epoxide.

21. A method according to claim 20, wherein said cationically photopolymerizable composition comprises 4-vinylcyclohexene dioxide, limonene dioxide, cyclohexene oxide, glycidyl phenyl ether, 3,4-epoxycyclohexylmethyl 3',4'-epoxycyclohexanecarboxylate, bis-2(3,4-epoxycyclohexylethyl)-1,3-tetramethyldisiloxane or a combination thereof.

22. A method according to claim 19, wherein said cationically photopolymerizable composition comprises 2-chloroethyl vinyl ether.

23. A composition comprising:
   a. a photosensitizing composition selected from the group consisting of:
      at least one polymeric photosensitizer comprising repeating units derived from at least one polymerizable compound comprising a polynuclear aromatic group capable of absorbing light having a wavelength ranging from 300 nm to 600 nm;

at least one siloxane comprising repeating units derived from a hydrosilation reaction between a SH-containing siloxane and at least one vinyl or allyl compound substituted with a polynuclear aromatic group capable of absorbing light having a wavelength ranging from 300 nm to 600 nm;
and combinations thereof;

b. at least one cationic photoinitiator comprising an onium salt; and c. a cationically photopolymerizable composition.

24. A composition according to claim 23, wherein said cationically photopolymerizable composition comprises an epoxide, an oxetane, a vinyl ether, a 1-propenyl ether or a combination thereof.

25. A composition according to claim 24, wherein said cationically photopolymerizable composition comprises at least one epoxide.

26. A composition according to claim 25, wherein said cationically photopolymerizable composition comprises 4-vinylcyclohexene dioxide, limonene dioxide, cyclohexene oxide, glycidyl phenyl ether, 3,4-epoxycyclohexylmethyl 3',4'-epoxycyclohexanecarboxylate, bis-2(3,4-epoxycyclohexylethyl)-1,3-tetramethyldisiloxane or a combination thereof.

27. A composition according to claim 24, wherein said cationically photopolymerizable composition comprises 1-chloroethyl vinyl ether.

28. A composition according to claim 23, wherein said cationic photoinitiator is chosen from the group consisting of triarylsulfonium salts, diaryliodonium salts, and dialkylphenacylsulfonium salts.

29. A composition according to claim 28, wherein said cationic photoinitiator is chosen from the group consisting of (4-n-decyloxyphenyl)phenyliodonium hexafluoroantimonate, (4-n-decyloxyphenyl)diphenylsulfonium hexafluoroantimonate, and S-dodecyl-S-methyl-S-phenacylsulfonium hexafluoroantimonate.

30. A composition according to claim 23 wherein said photosensitizing composition comprises a polymeric photo sensitizer.

31. A composition according to claim 30, wherein said polymeric photosensitizer comprises repeating units derived from an ethylenically unsaturated moiety.

32. A composition according to claim 31, wherein said polymeric photo sensitizer consists essentially of repeating units derived from 9-vinylcarbazole.

33. A composition according to claim 30, wherein said photosensitizer additionally comprises repeating units derived from at least one vinyl comonomer.

34. A composition according to claim 33, wherein said vinyl comonomer is selected from the group consisting of styrene, diethylfumarate, alkyl acrylate esters and alkyl methacrylate esters.

35. A composition according to claim 34, wherein said vinyl comonomer is diethylfumarate.

36. A composition according to claim 34, wherein said vinyl comonomer is butyl acrylate.

37. A composition according to claim 23, wherein said photosensitizing composition comprises 1,3-bis(2-carbazolylethyl)-1,1,3,3-tetramethyldisiloxane.

38. A polymeric photosensitizer derived from at least one polymerizable compound substituted with a polynuclear aromatic group selected from anthracene, perylene, pyrene, fluorene, indole, benzocarbazole, acridone, phenothiazine, or thianthrene, and capable of absorbing light having a wavelength ranging from 300 nm and 600 nm.

39. A polymeric photosensitizer according to claim 38, additionally comprising repeating units derived from at least one vinyl comonomer.

40. A polymeric photosensitizer according to claim 39, additionally comprising repeating units derived from at least one vinyl comonomer selected from the group consisting of styrene, diethylfumarate, and alkyl acrylate and methacrylate esters.

41. A polymeric photosensitizer according to claim 40, wherein said vinyl comonomer is diethylfumarate.

42. A polymeric photosensitizer according to claim 40, wherein said vinyl comonomer is butyl acrylate.

43. A polymeric photosensitizer according to claim 38, wherein said polymerizable photosensitizer is cis-9-(1-propenyl)carbazole.

44. A polymeric photosensitizer according to claim 38, wherein said polymerizable photosensitizer is trans-9-(1-propenyl)carbazole.

45. A polymeric photosensitizer according to claim 38, wherein said polymerizable photosensitizer is 9-(2-vinyloxyethyl)carbazole.

46. A polymeric photosensitizer according to claim 38, wherein said polymerizable photosensitizer is 9-(2,3-epoxypropyl)carbazole.

47. A composition comprising:
at least one polymerizable photosensitizer comprising a polynuclear aromatic group derived from anthracene, perylene, pyrene, fluorene, indole, benzocarbazole, acridone, phenothiazine, or thianthrene, and capable of absorbing light having a wavelength ranging from 300 nm and 600 nm;
at least one cationic photoinitiator comprising an onium salt; and
a cationically photopolymerizable composition.

48. A composition comprising at least one polymerizable photosensitizer, at least one cationic photoinitiator comprising an onium salt and at least one cationically photopolymerizable monomer;
wherein said at least one polymerizable photosensitizer is selected from the group consisting of:

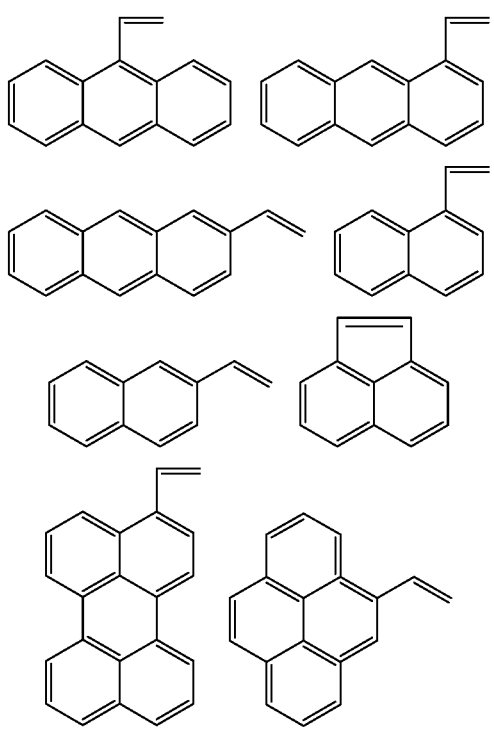

-continued
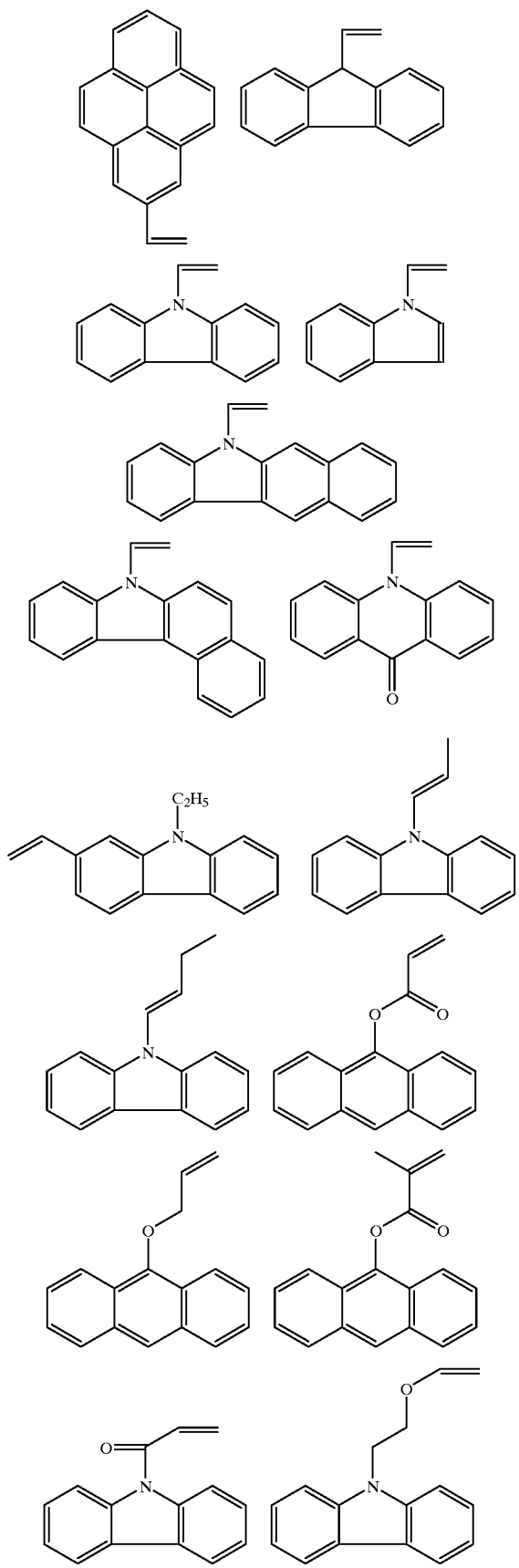
-continued
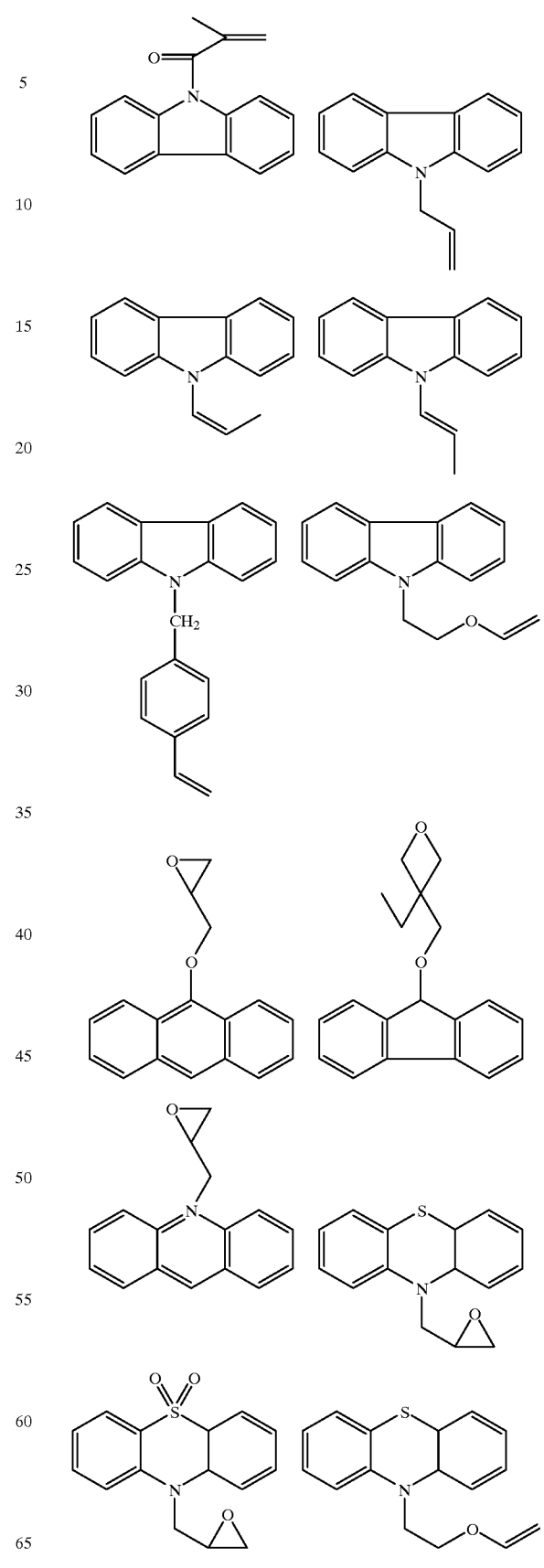

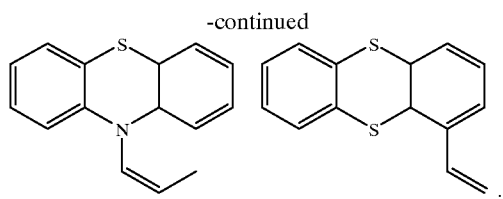

and combinations thereof.

49. A composition according to claim 48 wherein said polymerizable photosensitizer comprises cis-9-(1-propenyl)carbazole.

50. A composition according to claim 48 wherein said polymerizable photosensitizer comprises trans-9-(1-propenyl)carbazole.

51. A composition according to claim 48 wherein said polymerizable photosensitizer comprises 9-(2,3-epoxypropyl)carbazole.

52. A composition according to claim 48 wherein said polymerizable photosensitizer comprises 9-(2-vinyloxyethyl)carbazole.

* * * * *

UNITED STATES PATENT AND TRADEMARK OFFICE
CERTIFICATE OF CORRECTION

PATENT NO. : 6,593,388 B2
DATED : July 15, 2003
INVENTOR(S) : Crivello

It is certified that error appears in the above-identified patent and that said Letters Patent is hereby corrected as shown below:

<u>Title page,</u>
Item [73], Assignee, delete the state "MI" and insert -- NY --

Signed and Sealed this

Fourteenth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,593,388 B2
DATED : July 15, 2003
INVENTOR(S) : Crivello

It is certified that error appears in the above-identified patent and that said Letters Patent is hereby corrected as shown below:

<u>Title page,</u>
Item [73], Assignee, delete the word "Renssealer" and insert -- Rensselaer --

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

PATENT NO. : 6,593,388 B2  
DATED : July 15, 2003  
INVENTOR(S) : Crivello

It is certified that error appears in the above-identified patent and that said Letters Patent is hereby corrected as shown below:

<u>Title page,</u>
Item [73], Assignee, delete the "Renssealer" and insert -- Rensselaer --

Signed and Sealed this

Thirteenth Day of January, 2004

JON W. DUDAS
*Acting Director of the United States Patent and Trademark Office*